United States Patent [19]
Vasiloiu

[11] Patent Number: 6,087,132
[45] Date of Patent: Jul. 11, 2000

[54] MULTI-FUNCTIONAL ENZYMES INCLUDING DERIVABLE 2'3'-DIDEOXYRIBOFURANOSIDE TRIPROSPHATES

[76] Inventor: Roxana Vasiloiu, Auerfeldstr, 11, 6000, Frankfurt M. 60, Germany

[21] Appl. No.: 08/467,810

[22] Filed: Jun. 6, 1995

Related U.S. Application Data

[63] Continuation of application No. 07/838,703, filed as application No. PCT/DE90/00678, Sep. 6, 1990, abandoned.

[30] Foreign Application Priority Data

Sep. 12, 1989 [DE] Germany ............................. 39 30 441
Jun. 28, 1990 [DE] Germany ............................. 40 20 529

[51] Int. Cl.$^7$ ............................. C12P 19/30; C12P 19/28; C12P 19/38; C12P 19/40
[52] U.S. Cl. ............................. 435/89; 435/85; 435/87; 435/88; 435/91.1; 435/91.5
[58] Field of Search ................. 435/85, 88, 87, 435/91.1, 89, 91.5

[56] References Cited

U.S. PATENT DOCUMENTS 4,594,320  6/1986  Fujishima .................................. 435/89

FOREIGN PATENT DOCUMENTS

| 1223831 | 7/1987 | Canada . |
| 206497 | 12/1986 | European Pat. Off. . |
| 214014 | 3/1987 | European Pat. Off. . |
| 286425 | 10/1988 | European Pat. Off. . |
| 22006 | 3/1982 | Hungary . |
| WO 90 06312 | 11/1989 | WIPO . |

OTHER PUBLICATIONS

Papchi Khin et al., Bioorg. Khim., 11(10), 1367–79. 1985.
Huang et al., Abstract. 98:175460a Chemical Abstracts 98(21).
Seela et al., Synthesis, Sep. 1988, pp. 670–674.
Seela et al., Chem. Pharm. Bull., 36(10), 4153–56, 1988.
Carson et al., Biochemical & Biophysical Research Communications, vol. 155, No. 2, pp. 829–834, 1988.
Seela et al., Nucleosides & Nucleotides, 8(5&6), 789–792, 1989.
Schmidt et al., Liebigs Ann. Chem., (8), 1307–20, 1980.
Lessor et al., Biochemistry, 23, 3868–73, 1984.
Huang et al., Archives of Biochem. & Biophysics, vol. 222, No. 1, pp. 133–144, 1983.
Lindberg et al, J. Biol. Chem. 242(3):350–356, 1967.
Deibel et al, J. Biol. Chem. 252(22):8240–8244, 1977.
Ikeda et al, J. Biol. Chem. 261(34):15836–15843, 1986.
Chakravarty et al, Biochemistry 23:6235–6240, 1984.
Huang et al, Biochem. Pharmacol. 30(19):2663–2671, 1981.
Cardinaud et al, Biochem. J. 127(2):30P, 1972.
Cardinaud et al, Eur. J. Biochem. 54:505–514, 1975.
Blakely, Methods Enzymol., 51:246–259 (1978).
W. Fischer et al., "Enzymatic Procedure for the Synthesis of Base–Modified 2',3'–Dideoxynucleosides," *Dechema Biotechnology Conferences,* Bd. 3 Nr. Part A, pp. 183–187 (May, 1989).
J. Holguin et al., "Trans–N–Deoxyribosylase. Purification by Affinity Chromatography and Characterization," *Chemical Abstracts* 83(7), abstract no. 55084z, p. 199 (Aug., 1975).
S. Jyssum et al., "Search for Thymidine Phosphorylase, Nucleoside Deoxyribosyltransferase and Thymidine Kinase in Moraxella, Acinetobacter, and Allied Bacteria," *Biological Abstracts* 58(4), abstract no. 17637, p. 1882 (1974).
EPO Search Report for EPO application no. 97 11 5112.1, issued Oct. 31, 1997 (Den Haag).

*Primary Examiner*—Francisco Prats
*Attorney, Agent, or Firm*—Hall Priddy & Myers

[57] ABSTRACT

The invention relates to a multifunctional nucleoside didesoxyribosyl or nucleoside deoxyribosyl transferase which has one or more of the following additional activities (desoxy) nucleoside kinase, nucleoside reductase desaminase, or DNA polymerase activity. Utilizing the multifunctional enzyme results in a variety of nucleic acid products. These products can be prepared using sequential reactions in a single batch process wherein the sequential reaction can be caused to occur by varying process conditions in a manner which turns on or off the requisite activities causing the sequential reactions to occur. An example of a product prepared in this manner is dideoxyribofuranoside triphosphate. Certain of the resultant products have pharmaceutical activities, e.g. antiviral agents. *Lactobacillus leichmannii* (DSM 20076) is a source of the multifunctional nucleoside deoxyribosyl transferase.

9 Claims, 1 Drawing Sheet

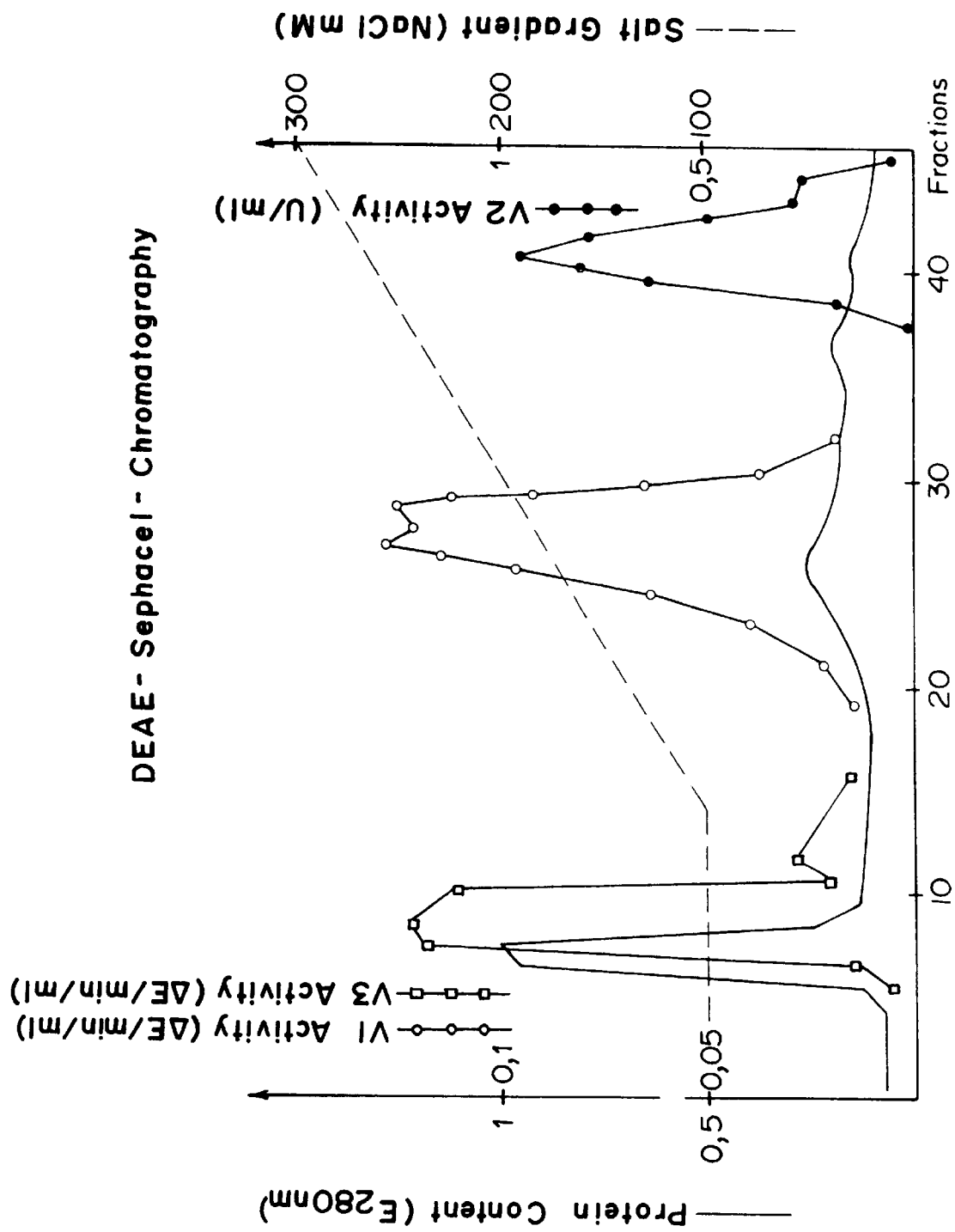

MULTI-FUNCTIONAL ENZYMES INCLUDING DERIVABLE 2'3'-DIDEOXYRIBOFURANOSIDE TRIPROSPHATES

This is a continuation of application Ser. No. 07/838,703, filed on Mar. 16, 1992, now abandoned, which is a 371 of PCT/DE90/00678, filed Sep. 6, 1990.

BACKGROUND

1. Field of the Invention

The subject of the present invention includes a plurality of multifunctional enzymes having a similar activity spectrum, which derive from the same or different microorganisms and cell materials, and a process for their preparation, along with uses, and processes using the multifunctional enzymes.

The invention relates to at least one novel nucleoside deoxyribosyl transferase, in particular of *Lactobacillus leichmannii*, to a process for its purification, to the multi-functionality of the nucleoside deoxyribosyl transferase I, II, III (V 1, V 2, V 3), each of which has kinase, reductase, deaminase and polymerase activity, and to an enzyme technology process for preparing a wide range of base-modified nucleosides, nucleotides, and polynucleotides.

2. Description of Related Art

It is known that the microorganism *Lactobacillus leichmannii* has two nucleoside deoxyribosyl transferases, V 1 (DRTI, which as yet has no EC number) and V 2 (DRT II) (EC 2.4.2.6), which catalyze the transfer of 2'-deoxyribose from a pyrimidine (purine) nucleoside to a purine (pyrimidine) base:

dRib-Pur+Pur' ⇌ dRib-Pur'+Pur (V 1) dRib-Pyr(Pur')
(Pur)+Pyr'(Pur') ⇌ dRib-Pyr'+Pyr(Pur) ††
dRib-Pyr+Pur ⇌ dRib-Pur+Pyr (V 2)

Abbreviations: Pur: purine base
Pyr: pyrimidine base
dRib: 2'-deoxyribose

SUMMARY OF THE INVENTION

Surprisingly, during the process of purifying the already known enzymes V 1 and V 2 from *Lactobacillus leichmannii*, a third nucleoside, deoxyribosyl transferase V 3, was discovered, which catalyzes the following reaction:

drib-Pur+Pur' ⇌ dRib-Pur'+Pur

The three multifunctional enzymes were purified from Lactobacillus via two prepurification steps and ion exchange chromatography (in which the three proteins were separated from one another with good resolution). Each protein was further purified via affinity chromatography.

In this way, V 1, V 2 and V 3 were purified to the point of homogeneity.

The subunit structure of the three enzymes was studied by SDS pore gradient electrophoresis. V 1 and V 2 each comprise two subunits, of 19 and 20 kilodaltons each and V 3 comprises a single 20-kilodalton polypeptide chain.

V 1, V 2 and V 3 are allosteric enzymes, which form aggregates. With increasing ion strength or solvent concentration, or in lyophilization, they can clump together to form larger aggregates (dimers, trimers, and so forth), which has been demonstrated by electrophoresis.

Both the new enzyme and the known ones not only have transferase activity but also kinase, reductase, deaminase and polymerase activities.

All these activities are located on the same polypeptide chain, and cannot be separated by the known (preparative and analytic) biochemical process, such as affinity chromatography, electrophoresis, and isofocusing. Separation could possibly be performed by nonspecific proteolysis.

Furthermore, all these activities have inhibitors and activators in common, which is further proof that the active centers for all these functions are components of polyprotein.

In multifunctional enzymes, all activities cannot always be demonstrated.

Transferase Activity

V 3 is capable of catalyzing the transfer of a 2'-deoxy(2', 3'-dideoxy)ribofuranosyl residue from a 2'-deoxy(2',3'-dideoxy) ribonucleoside to a purine base, forming 2'-deoxy (2',3'-dideoxy)ribofuranosides (Examples 2, 3).

The enzymatic activity was determined by the following two methods:

Direct Spectrophotometric Method

This method is based on the greater extinction of the synthesized 6-chloro-2'-deoxyguanosine at 305 nm in comparison with the acceptor base used, 6-chloroguanine ($^\epsilon 305$ nm–760 $m^{-1} \cdot cm^{-1}$, where $\epsilon$- molar coefficient of extinction).

In the reaction mixture, 1 mM of 2'-deoxyadenosine or 2'-deoxyinosine and 0.2 mM of 6-chloroguanine are used.

One activity unit has been defined as an increase in absorption of 0.01 absorption units at 305 nm/37° C./min/ml.

Method of R. Cardinaud (Methods in Enzymology, vol. LI)

In a reaction mixture with 0.3 M of phosphate buffer at pH 6.0, 1 mM of 2'-deoxyinosine, 1 mM of acceptor base, and 50 μL of xanthine oxidase (10 mg/ml in 3.2 M of $(NH_4)_2 SO_4$ made by Boehringer, Mannheim, diluted 1:10 with 2 M $(NH_4)_2 SO_4$, the hypoxanthine that occurs after the transfer of the deoxyribose from 2'-deoxyinosine is oxidized from the auxiliary enzyme to xanthine and further to uric acid. Uric acid has an absorption maximum at 290 nm.

The first method has the advantage that the nucleoside can be varied arbitrarily, while in the second method various acceptor bases can be tested.

Analytically, the course of the transfer reaction, as well as that of the phosphorylation, reduction, deamination and polymerization, were pursued by HPLC chromatography. The reversed-phase matrix comprised octadecylsilane. As the eluting agent 50 mM of $KH_2PO_4$ was used, and the methanol concentration varied between 2.5% and 50%, depending on how hydrophobic the product was.

V 3 particularly recognizes 1-, 7-, 8- and 3-substituted purines as acceptor bases, while V 2 predominantly recognizes the 2- and 6-substituted ones.

With the aid of V 3, it is possible to prepare the following 2',3'-dideoxyribofuranosides:

1,7-dimethylguanin-9-β-D-2', 3-didesoxyribofuranoside

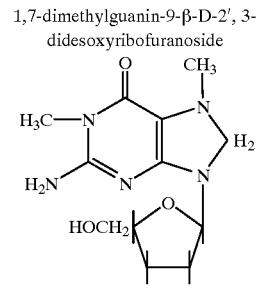

-continued 1-hydroxyisoguanine-9-β-D-2', 3' didesoxyribofuranoside

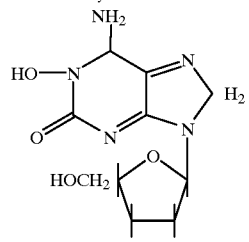

8-methylxanthin-9-β-D-2', 3' didesoxyribofuranoside

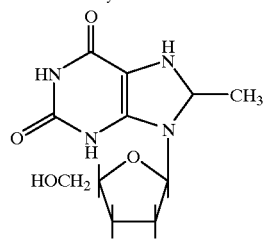

2-hydroxypurine-9-β-D-2', 3'-didesoxyribofuranoside

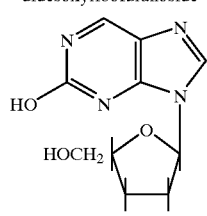

1-methyladenine-9-β-D-2', 3'-dideoxyribofuranoside

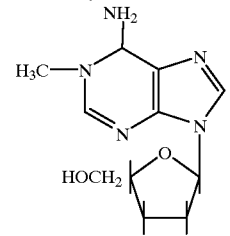

Benzimidazole-1-β-D-2', 3'-didesoxyribofuranoside

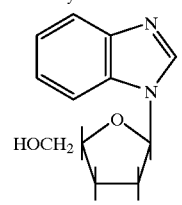

7-dimethylguanine-9-β-D-2', 3 dideoxyribofuranoside

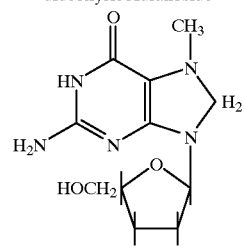

For detecting the 2', 3'-dideoxyribofuranosides, both spectrophotometric measurements by the above methods and HPLC analyses were performed. The following elution program was employed:

| | |
|---|---|
| 0 to 10 minutes | 0 to 100% buffer B |
| 10 to 25 minutes | 100% buffer B |
| 25 to 28 minutes | 100 to 0% buffer B |
| 28 to 30 minutes | 0% buffer B |

Buffer A: 50 mM $KH_2PO_4$ 2.5% MeOH buffer B: 50 mM $KH_2PO_4$

50% MeOH

Column dimensions: 4×250 mm

Flow rate: 1 ml/min

Under these conditions, the compounds exhibited the following retention times:

| | |
|---|---|
| 1,7-dimethylguanine-ddr | 14.8 or 16.2 min |
| 1-hydroxyisoguanine-ddr | 5.4 min |
| 8-methylxanthine-ddr | 13.6 min |
| 1-methyladenine-ddr | 6.7 min |
| 2-hydroxypurine-ddr | 7.7 min |

The reaction speed was 15 to 20 nmol/min/unit of enzyme. At concentrations of above 1 mM, the ddA (ddr donor) has an inhibiting effect.

The 2',3'-dideoxyribofuranosides has a pronounced potential in chemotherapy, in particular as antiviral agents.

All of the above-named 2', 3'-dideoxyribofuranosides can be phosphorylated by the kinase activity, to make the corresponding triphosphates.

Kinase Activity

The enzymes V 1, V 2 and V 3 of *Lactobacillus leichmannii* catalyze the transfer of an inorganic phosphate group from a nucleotide (phosphate donor) to a nucleoside or nucleotide (acceptor).

The phosphate acceptor can be phosphorylated in stages, via the monophosphate and diphosphate deoxynucleotides or dideoxynucleotides or nucleotides or their analog, to make the triphosphate deoxynucleotides, or dideoxynucleotides or nucleotides or their analog (Examples 4, 5).

The substrate specificity of V 1, V 2 and V 3, relating to acceptors of the phosphorylation reaction is as follows:

| Enzyme | Substrate |
|---|---|
| V 1 | dC, dG, dA, the corresponding nucleotides and analogs |
| V 2 | dG, dA, dC, dT, the corresponding nucleotides and analogs |
| V 3 | dT, dC, dG, dA, the corresponding nucleotides and analogs |

The efficiency of the various phosphate donors vary (nucleotides) as a function of the acceptor, and can be found in the following table:

| Substrate | Donor | Efficiency (in %) |
|---|---|---|
| dT | dATP | 100 |
| dG | ATP | 52 |
| dC | CTP | 18 |
| dA | dCTP | 100 |
|    | dGTP | 76 |
|    | CTP | 45 |
|    | ATP | 39 |
|    | GTP | 20 |

A wide variety of acceptors is possible because of the wide substrate spectrum of V 1, V 2 and V 3.

Reductase Activity

The enzymes V 1, V 2 and V 3 can catalyze the reduction of nucleotides, in the presence of a coenzyme and an effector.

Substrates that can be used for the reaction are ATP, CTP, GTP and UTP, and their di- and/or mono-phosphates and their analog (Example 6).

For efficient reaction speeds, it is absolutely necessary that the effectors and the coenzyme B12 be present.

Few reductions occur in the absence of the effectors. The coenzyme B12 is commercially available, for instance from Fluka AG, Federal Republic of Germany. Concentrations of coenzyme B12 of above 50 mM or concentrations of 15 to 20 mM in the presence of 10 mM of 5'-deoxyadenosine inhibit all the activities of the multifunctional enzyme. The following effectors are necessary in the reductions reaction:

| Substrate | Effector |
|---|---|
| ATP | dGTP |
| CTP | dATP |
| UTP | dCTP |
| GTP | dTTP |

A reduction in the mono- and di-phosphate plane is also possible.

Deaminase Activity

The enzymes V 1, V 2 and V 3 catalyze the hydrolysis of the amino group of nucleotides, nucleosides, and purine and pyrimidine bases.

To carry out the demination successfully, the reaction mixtures must be incubated for a relatively long time at 37° C. until the reaction ensues. For example, 2'-deoxyuridine is formed from 2'-deoxcytidine, and 2',3'-dideoxyinosine is formed from 2',3'-dideoxyadenosine (Examples 7, 8).

A so-called lag phase (no reaction occurs in the first several hours) is a typical behavior of multifunctional enzymes and is ascribed to a change in conformation.

Nucleosidase Activity

Enzymes V 1, V 2 and V 3 also have the capability of hydrolyzing the glycoside bond of the nucleosides. Just as the deamination reaction, the hydrolysis has a lag phase.

Polymerase Activity

The multifunctional enzymes from Lactobacillus, V 1, V 2 and V 3, which simultaneously have transferase, reductase, deaminase and kinase activity, are also capable of catalyzing the conversion of dideoxyribonucleotides, producing homo- or hetero-polymers. This is a de novo polymerization activity. The linkage of the nucleotides takes place in all phosphorylation planes. Not only triphosphate but also diphosphate and monophosphate deoxynucleosides are incorporated in polymers. The de novo polymerization also has a lag phase of 20 to 70 hours (Example 9).

This capability has already been noted by J. P. Durham and D. H. Ives, who worked on the deoxynucleoside kinase activity of the multifunctional enzymes, but they were unable to identify the end product (1).

A multifunctionality of the deoxyribonucleoside kinases was already derived from kinetic studies in 1977 (2, 3, 4). It was found that the phosphorylation of deoxyadenosine and deoxyguanosine takes place at two different active centers of a single polypeptide (5).

These polyproteins can be defined as a polypeptide chain (product of a single gene) with two or more active centers (6).

Of the three multifunctional enzymes from Lactobacillus, V 1, V 2, V 3, only the last two exhibit de novo polymerase activity, but all three catalyze the replication of a template, such as poly[d(A-T)] (Examples 10, 11).

The three enzymes from Lactobacillus catalyze the replication of various natural and synthetic DNAs—double-stranded, single-stranded, annular, denatured—with various efficiencies. The ribonucleotides are polymerized with an efficiency of 2 to 3% of the incorporation rate of the deoxyribonucleotides.

In Lactobacillus, there is probably also a fourth multifunctional enzyme that is involved in the DNA replication. However, because of its great instability, it has not yet been possible to isolate and purify it.

It is known that DNA polymerases have six highly preserved sequences, which remain unaltered over hundreds of millions of years (9, 11, 15, 16). For this reason, the corresponding enzymes of other organisms were tested for the same activities.

On being purified to homogeneity, by a modified method of Pfrogner (14) adenosine deaminase from calf spleen (Worthington Biochemical Corporation, Lot No. 59P412) exhibits similar properties. The enzyme was purified 500 times by isoelectric precipitation, ammonium sulfate precipitation, and chromatography done with Bio-Rex-70, DEAE-Sephadex A-50, SE-Sephadex C-50 (the last two steps were repeated). The publication presents evidence that the adenosine deaminase would be homogeneous.

The multifunctional enzyme from calf spleen catalyzes the reduction of ADP and UDP (in the presence of effectors and NADPH), the phosphorylation of dAMP and dCMP (with a corresponding phosphate donor), de novo polymerization of the nucleotides, and the replication of a template (Example 12).

The *E. coli* DNA polymerase I (Pharmacia 27-0626) *E. coli* CM 5197), an enzyme already known to be multifunctional (the polymerase and the 3'-5'-exonuclease activity belong to the same polypeptide chain and can be split off only proteolytically) has still other, as yet unsuspected, capabilities.

It deaminates 2'-deoxyadenosine to make 2'-deoxyinosine (Example 13), and reduces ADP to dADP in the presence of dGTP and NADPH. The multifunctional enzyme from *E. coli* is also active as a nucleoside diphosphate kinase. This last activity has also been observed by A. Kornberg (17).

The DNA polymerase from *Micrococcus luteus* (Sigma Chemie GmbH D 2626) exhibits similar properties (7), and is capable of deaminating and phosphorylating adenosine (Examples 14, 15). The reduction of CTP was studied by spectrophotometry (decrease in absorption of NADPH at 340 nm), and by HPLC analyses.

Polyclonal rabbit antibodies to V 2 and V 3 exhibit a positive cross reaction with *E. coli* DNA polymerase I, in an ELISA test on a microtiter slide.

The immunological affinity between V 3 and polymerase I is very high. Structurally as well, the two enzymes are quite similar: They comprise a monomer and have a plurality of active centers or activities, as part of a single polypeptide. Immunoglobulins G to V 2 also, to a certain extent, exhibit a positive cross reaction with polymerase I.

The phenomenon (the association of the aforementioned activities) is also confirmed in other organisms and appears to be universal.

For example, in the calf intestine, four adenosine deaminases have already been detected (20), which are part of the multifunctional enzymes described herein and probably also have the other activities that the adenosine deaminase from calf spleen has.

Unpublished results from studies of 2',3'-dideosyadenosine metabolism in human cells reinforce the hypothesis. In the deoxycytidine kinase- and deoxyadenosine kinase-deficient T-lymphocytes, a deamination rate of ddA at the level of only 25% compared with the wild type is recorded. this can be explained as follows: The dCK~ and dAK~ cells are deficient in two multifunctional enzymes, with all their activities (kinase, reductase, deaminase, polymerase), which explains the low deamination rate.

The discovery of the multifunctional enzymes that are involved in DNA replication would also explain the following fact: Viral T 7 DNA polymerase requires a thioredoxin molecule from the host cell (*E. coli*) in order to become active at all. The thioredoxin also functions in this case a redox coenzyme for the reduction of the nucleotides. A. Kornberg was unable to explain why a DNA polymerase requires a thioredoxin molecule (17, 18). A primase activity of DNA polymerase α from human cells has already been demonstrated. The enzyme is currently called "polymerase primase" for that reason. The name describes only two of all the activities that the enzyme has (19).

The 3'-5'-exonuclease in some such multifunctional enzymes is already known.

It is also known that extraordinary difficulties arise during the process of purifying these enzymes, because of nonspecific proteolysis and aggregate formation. In vivo, the aggregate formation reinforces the allostery of these regular enzymes (8, 9, 10, 12, 13, 17).

The usual protease inhibitors, such as phenylmethylsulfonyl fluoride, do not influence nonspecific proteolysis. Special inhibitors such as antipain, leupeptin, aprotinin, etc. (12), inhibit both the proteases and the polymerase activity of the multifunctional enzymes.

Reverse transcriptase (RNA-dependent DNA polymerase) is quite similar to other polymerases and even has DNA-dependent DNA polymerase activity. It is a fusion protein, currently called integrase, which has protease, reverse transcriptase, RN-ase H, and endonuclease activities (21, 22). Even the six highly preserved, functional regions of the DNA polymerases can also be identified in the reverse transcriptases (22).

These facts suggest that "all these multifunctional enzymes have developed from a common ancestral gene" (16).

Applications of the Multifunctionality of V 1, V 2 and V 3

The various activities of the multifunctional enzymes can be employed individually for purposes of producing the base-modified nucleosides, nucleotides and poly(oligo) nucleotides; the substrate specificity of the Lactobacillus enzyme is substantially wider, in virtually all activities, than that of the corresponding enzymes from *E. coli* or calf spleen. In those, the reduction of the nucleotides occurred only in the diphosphate plane, and they have only nucleoside diphosphate kinase activity. Only a few other organisms have multifunctional enzymes with such a wide substrate spectrum.

The advantage that arises from the multifunctionality is that an entire reaction sequence, as occurs with a high efficiency in vivo can be carried out with the aid of such an enzyme.

For example, the nucleoside kinase activity can be coupled with either the de novo polymerase activity or the polymerization of a template. De novo polymerization takes place spontaneously after phosphorylation, but only through prolonged incubation at 35° C. Heteropolymers are produced (Examples 16, 17).

Homopolymers are prepared through de novo polymerization of a single nucleotide (Example 9). V 2 and V 3 are capable of linking nucleotides in all phosphorylation planes.

In the case of phosphorylation of a nucleoside followed by polymerization of a template, the substrates of the second reaction are not presented to the enzyme until the first reaction has attained equilibrium. (Example 18)

The deoxyribose transfer reaction can readily be combined with the phosphorylation and polymerization reactions.

Alternatively, the reduction of the nucleotides can be followed (directly) by the phosphorylation (Example 19).

The most important applications of V 1, V 2 and V 3, which are distinguished by high economy, are as follows:

Synthesis of the novel 2', 3'-dideoxyribonucleosides, whose preparation had until now been impossible.

The highly efficient phosphorylation of the 2',3'-dideoxyribonucleoside(s) to triphosphate(s), which could until now only be accomplished by an expensive chemical and enzymetechnological procedure.

Enzymatic synthesis of homo- and heteropolynucleotides. An advantage in preparing homopolymers by de novo polymerization is that no primer is needed for initiating the synthesis, and that the substrate is consumed up to 100%, which considerably simplifies the purification of the process.

The use of V 3 (or V 1, V 2) in the DNA-sequencing method of Sanger (23). The fact that Lactobacillus enzymes have the capability of incorporating ddNDP or ddNMP (instead of expensive ddNTP) has major financial advantages.

This application has additional special significance in view of the human genome sequencing program.

Repeated use of a biological catalyst for many reactions considerably reduces the costs of preparation of the end products.

The following facts make the synthesis of a wide range of modified nucleosides, nucleotides and polynucleotides possible, which could not be synthesized until now:

a) the wide substrate spectrum of the three multifunctional enzymes from *Lactobacillus leichmannii*;

b) the substrate specificity of the multifunctional enzymes of other prokaryotic and eukaryotic cells;

c) the unsuspected specificities of new enzymatic activities, which by using this theory can be detected purposefully and systematically.

BRIEF DESCRIPTION OF THE DRAWING

FIG. 1 is an elution profile of three *Lactobacillus leichmannii* nucleoside deoxyribosyl transferases, the enzymes being eluted from a DEAE Sephacel column using an NaCl gradient.

DESCRIPTION OF THE PREFERRED EMBODIMENTS

EXAMPLE 1

150 l MRS-medium are inoculated with 1 l of a logarithmic preculture of *Lactobacillus leichmannii* (DSM 20076).

DSM refers to Deutsche Sammlung von Mikroorganismen and Zellkulturen GmbH located at Mascheroder Weg 1b, D-3300 Braunschweig, Federal Republic of Germany. The microorganisms were stirred at 37° C., anaerobically until they attained the steady phase (approximately 6 hours). With cross-flow filtration equipment, the cell suspension was concentrated and then centrifuged off. The yield was 12.5 g/l wet cell weight.

MRS Medium

| MRS Medium | |
|---|---|
| Peptone for bacteriology | 10 g |
| Meat extract | 5 g |
| Yeast extract | 5 g |
| $K_2HPO_4$ | 2 g |
| Sodium citrate | 2 g |
| Sodium acetate × 3 $H_2O$ | 6 g |
| $MgSO_4$ × 7 $H_2O$ | 0.58 g |
| $MnSO_4$ × 4 $H_2O$ | 0.28 g |
| Tween 80 | 1 g |
| Glucose | 20 g |

Water ad 1 l, adjust pH with HCl 1 N to 6.2–6.3

20 g dells (wet weight) were disintegrated in 30 ml buffer and 80 g of glass beads (diameter 0.75 mm) at 4000 rpm in a glass bead disintegrator. Disintegration lasted no longer than 5 min.

Disintegration Buffer

| Disintegration Buffer | |
|---|---|
| Phosphate buffer (Na) | 20 mM, pH 6.5 |
| NaCl | 50 mM |
| EDTA | 0.1 mM |
| Mercaptoethanol | 1 mM |

PMSF (phenylmethylsufonyl fluoride) 20 µM

The crude extract obtained, with an optimal protein concentration of 10 mg/ml) is mixed, while stirring, at 4° C. with 1% (wet weight) protamine sulfate solution, pH 6.5, for one hour, until a final concentration of protamine sulfate of 0.4 to 0.45% is attained. The proteins that have settled out are centrifuged at 11,000 rpm for 15 minutes. Following this precipitation, relatively large aggregates of the proteins are formed, as a result of which a 30% increase in activity of V 2 is effected.

This is followed by a first ammonium sulfate precipitation between 0 and 50% saturation; that in turn is followed by a second ammonium sulfate precipitation at between 50 and 70% saturation. In the last saturation range, the transferase precipitate out.

The nucleoside deoxyribosyl transferase were separated from one another in a DEAE-Sephacel column, which was equilibrated with 20 mM of phosphate buffer, 100 mM NaCl, 0.1 mM EDTA, 1 mM mercaptoethanol. On the NaCl gradient, V 1 is eluted between 160 and 190 mM, V 2 between 260 and 280 mM, and V 3 at the end of the breakdown with 100 mM of NaCl (see FIG. 1).

The fractions that show transferase activity were combined and dialyzed with 20 mM tris-HCl, pH 7.0, 20 mM KCl, 4.0 mM DTT, 4.0 mM $MgCl_2$, 0.1 mM EDTA. 3 ml 5-AMP agarose (affinity matrix) were packed in a column and equilibrated with the aforementioned buffer. The sample (5 ml) containing V 3 was recirculated for one hour through the column by means of a peristaltic pump (flow rate 10 ml/h). The unbound enzyme was washed with 4 column volumes of 100 mM KCL in the same buffer. The V 3 is not eluted until a concentration of 300 mM of KCl in the tris-HCl buffer is reached.

By this purification process, it was possible to increase the specific activity of V 3 to 20 units per milligram of protein. A homogeneous protein is therefore present.

It was possible to isolate the following quantities of enzyme from the cells, per gram of wet cell weight:

| V 1 | 50 µg (1 unit) |
|---|---|
| V 2 | 160 µg (2–7 units) |
| V 3 | 550–600 µg (11–12 units) |

Examples for the Transferase Activity of V 3

EXAMPLE 2

Transferase activity was demonstrated for V3 enzyme obtained in a manner as described in Example 1 by reacting a suitable quantity of the enzyme under the conditions described below.

Phosphate buffer (Na) 20 mM, NaCl 50 mM, pH 6.2

2',3'-dideoxyadenosine 0.2 mM 1,7-dimethylguanine 0.1 mM

V 3 10 U/ml reaction mixture

Temperature: 35 to 37° C.

Duration of reaction to equilibrium: 3 to 5 days

End product: 1,7-dimethylguanine-9-β-D-2',3'-dideoxyribofuranoside.

Here, the ddr is transferred to both position N 9 and position N 3.

In the same fashion a 2',3'-dideoxyribosyl residue is transferred to the following:

1-hydroxyisoguanine 8-methylxanthine 2-hydroxypurine 1-methyladenine 7-methylguanine Benzimidazole

EXAMPLE 3

Transferase activity was demonstrated for V3 enzyme obtained in a manner as described in Example 1 by reacting a suitable quantity of the enzyme under the conditions described below.

| Phosphate buffer (sodium) | 20 mM, NaCl 50 mM, pH 6.2 |
|---|---|
| 2'-Deoxyinosine | 2 mM |
| 8-Bromguanine | 0.5 mM |
| V 3 | 5 U/ml reaction mixture |
| Temperature: 35–37° C. | |
| Duration of reaction time: 24 to 30 hours | |
| End product: 8-bromguanosine | |

Examples for the Kinase Activity of V 1, V 2 and V 3

EXAMPLE 4

Kinase activity was demonstrated for V 3 enzyme obtained in a manner as described in Example 1 by reacting a suitable quantity of the enzyme under the conditions described below.

| | |
|---|---|
| Buffer: tris-chloride | 50 mM, pH 7.2 |
| MgCl$_2$ | 6.5 mM |
| Dithiotreitol (DTT) | 2.5 mM |
| Adenosine 5'-triphosphate | 5 mM |
| 2'-Deoxythymidine | 3 mM |
| V 3 | 5 U/ml reaction mixture |
| Temperature: 35–37° C. | |
| End products: dTMP, dTDP, dTTP (traces). | |

EXAMPLE 5

Kinase activity was demonstrated for V3 enzyme obtained in a manner as described in Example 1 by reacting a suitable quantity of the enzyme under the conditions described below.

| | |
|---|---|
| 2'-Deoxycytidine 5'-triphosphate | 5 mM |
| 2',3'-Dideoxyadenosine | 3 mM |
| Buffer tris-HCl | 50 mM, pH 7.2 |
| MgCl$_2$ | 6.5 mM |
| DTT | 2.5 mM |
| V 3 | 10/U/ml reaction mixture |
| Temperature: 35–37° C. | |
| Equilibrium is reached in 5–7 days. | |
| End products: ddAMP, ddADP, ddATP | |

In the same fashion as above
  1,7-dimethylguanine-9-β-D-2',3'-dideoxyribofuranoside
  1-hydroxy-iso-guanine-9-β-D-2',3'-dideoxyribofuranoside
  8-methylxanthine-9-β-D-2',3'-dideoxyribofuranoside
  2-hydroxypurine-9-β-D-2',3'-dideoxyribofuranoside
  1-methyladenine-9-β-D-2',3'-dideoxyribofuranoside
  7-methylguanine-9-β-D-2',3'-dideoxyribofuranoside
  benzimidazole-1-β-D-2',3'-dideoxyribofuranoside
are phosphorylated.
Examples for the Reductase Activity of V 1, V 2 and V 3

EXAMPLE 6

Reductase activity was demonstrated for V 1, V 2, and V 3 enzymes obtained in a manner as described in Example 1 by reacting a suitable quantity of each enzyme under the conditions described below.

| | |
|---|---|
| Buffer: sodium acetate | 60 nM |
| K$_2$HPO$_4$ | 3 mM |
| ATP (ADP or AMP) | 1 mM |
| Coenzyme B 12 | 4 μM |
| DTT | 30 mM |
| dGTP (effector) | 1 mM |
| Enzyme (V 1, V 2, V 3) units/ml of reaction mixture | 0.2 to 0.5 |
| Duration of the reaction: | 2 to 3 days |
| End product: dATP (dADP or dAMP) | |

Example for the Deaminase Activity of V 1, V 2 and V 3

EXAMPLE 7

Deaminase activity was demonstrated for V2 enzyme obtained in a manner as described in Example 1 by reacting a suitable quantity of the enzyme under the conditions described below.

| | |
|---|---|
| Phosphate buffer 20 mM, NaCl | 50 mM, pH 6.5 |
| 2'-deoxycytidine | 2 mM |
| V 2 0.5 U/ml reaction mixture | |
| End product: 2'deoxyuridine | |

EXAMPLE 8

Deaminase activity was demonstrated for V3 enzyme obtained in a manner as described in Example 1 by reacting a suitable quantity of the enzyme under the conditions described below.

| | |
|---|---|
| Phosphate buffer 20 mM, NaCl | 50 mM, pH 6.5 |
| 2',3'-Dideoxyadenosine | 2 mM |
| V 3  5 U/ml reaction mixture | |
| End product: 2',3'-dideoxyinosine | |

The reaction mixtures must be incubated for a relatively long time at 37° C. before the deamination occurs. The duration of the deamination reactions is 2 to 4 days.

EXAMPLE 9
De Novo Polymerization

De novo polymerase activity was demonstrated for either V2 or V3 enzyme obtained in a manner as described in Example 1 by reacting a suitable quantity of the enzyme under the conditions described below.

| | |
|---|---|
| Buffer: tris-HCl | 60 mM, pH 7.2 |
| DTT | 2.5 mM |
| dATP | 5 mM |
| Enzyme: V 3 (V 2) | 5 U/ml (1 U/ml) reaction mixture |
| Temperature: 35° C. | |
| Duration of the reaction: 3 days | |
| Product: poly(dA) | |

EXAMPLE 10
Example for Replication of Poly [d(A-T)]

Polymerase activity was demonstrated for any one of V1, V2 or V3 enzyme obtained in a manner as described in Example 1 by reacting a suitable quantity of the enzyme under the conditions described below.

| | |
|---|---|
| Buffer: tris-HCl | 40 mM, pH 7.55 |
| MgCl$_2$ | 5 mM |
| DTT | 1 mM |
| BSA | 50 μg/ml |
| Poly [d(A–T)] | 1.5 A260 U |
| dATP | 1 mM |
| dTTP | 1 mM |
| dGTP | 1 mM |
| dCTP | 1 mM |
| Enzyme: V 1, V 2, V 3 | 2 to 5 U/ml reaction mixture |
| Temperature: 35–37° C. | |
| Duration of the reaction: 3 to 5 days | |
| Product: poly [d(A–T)] | |

EXAMPLE 11

Polymerase activity was demonstrated for V3 enzyme obtained in a manner as described in Example 1 by reacting a suitable quantity of the enzyme under the conditions described below.

| Buffer: tris-HCl | 40 mM, pH 7.2 |
| DTT | 2.5 mM |
| dAMP | 1 mM |
| MgCl$_2$ | 6.5 mM |
| BSA | 50 μg/ml |
| Poly [d(A–T)] | 1.5 A260 U |
| dTTP | 1 mM |
| dGTP | 1 mM |
| dCTP | 1M |
| Enzyme: V 3 | 5 units/ml of reaction mixture |
| Temperature: 35° C. | |
| Duration of the reaction: 3 to 5 days | |
| Product: poly [d(A–T)] | |

Examples for the Multifunctionality of Similar Enzymes from Other Organisms

EXAMPLE 12

Multifunctionality of adenosine deaminase obtained from calf spleen was demonstrated by reacting a suitable quantity of deaminase under the conditions described below.

| Buffer: tris-HCl | 100 mM, pH 7.5 |
| dAMP | 1 mM |
| dCTP | 2 mM |
| MgCl$_2$ | 10 mM |
| DTT | 1 mM |
| BSA | 100 μg/ml |
| Enzyme: adenosine deaminase from calf spleen | 2 units/ml of reaction mixture |
| Temperature: 35° C. | |
| Duration of the reaction: 2 to 30 hours | |
| Product: dADP, dATP | |

EXAMPLE 13

Multifunctionality of adenosine deaminase obtained from E. coli was demonstrated by reacting a suitable quantity of deaminase under the conditions described below.

| Buffer: phosphate | 50 mM, pH 6.2 |
| dA | 2 mM |
| Enzyme: DNA-polymerase I from E. coli | 2 units/ml of reaction mixture |
| Temperature: 37° C. | |
| Duration of the reaction: 5 days | |
| Product: dI, hypoxanthine | |

EXAMPLE 14

Multifunctionality of DNA-polymerase obtained from Micrococcus luteus was demonstrated by reacting a suitable quantity of polymerase under the conditions described below.

| Buffer: phosphate | 50 mM, pH 6.2 |
| dA | 2 mM |
| BSA | 50 μg/ml |
| Enzyme: DNA-polymerase from Micrococcus luteus | 1 unit/ml of reaction mixture |
| Temperature: 35° C. | |
| Duration of reaction: 20 to 24 hours | |
| Products: dI, hypoxanthine | |

EXAMPLE 15

Multifunctionality of DNA-polymerase obtained from Micrococcus luteus was demonstrated by reacting a suitable quantity of polymerase under the conditions described below.

| Buffer: tris-HCl | 100 mM, pH 7.5 |
| dA | 3 mM |
| dCTP | 5 mM |
| MgCl$_2$ | 5 mM |
| DTT | 2.5 mM |
| BSA | 50 μg/ml |
| Enzyme: DNA-polymerase from Micrococcus leteus | 1 unit/ml of reaction mixture |
| Temperature: 35° C. | |
| Duration of the reaction: 2 days | |
| Products: dAMP, dADP, dATP | |

Examples for Reaction Sequences

EXAMPLE 16

Reaction Sequences utilizing the multifunctionality of the V 3 enzyme obtained in a manner as described in Example 1 by reacting a suitable quantity of the enzyme under the conditions described below.

| Buffer: tris-HCl | 40 mM, pH 7.55 |
| MgCl$_2$ | 6.5 mM |
| DTT | 2.5 mM |
| dATP | 5 mM |
| dC | 3 mM |
| Enzyme V 3 | 5 U/ml reaction mixture |
| Temperature: 35° C. | |
| Duration of the reaction: 2 days | |
| Products: dCMP, dCDP | |
| A spontaneous de novo polymerization occurs in the next 3 days. | |
| Product: poly (dA–dC) | |

EXAMPLE 17

Reaction sequences utilizing the multifunctionality of the V 2 enzyme obtained in a manner as described in Example 1 by reacting a suitable quantity of the enzyme under the conditions described below.

| Buffer: tris-HCl | 40 mM, pH 7.55 |
| MgCl$_2$ | 6.5 mM |
| DTT | 2.5 mM |
| dATP | 5 mM |
| dG | 3 mM |
| Enzyme: V 2 | 1 unit/ml of reaction mixture |
| Temperature: 35° C. | |
| Duration of the reaction: 2 days | |
| After de novo-polymerization, poly (dA–dG) occurs. | |

EXAMPLE 18

Reaction sequences utilizing the multifunctionality of the V 3 enzyme obtained in a manner as described in Example 1 were demonstrated by reacting a suitable quantity of the enzyme under the conditions described below.

| | |
|---|---|
| Buffer: tris-HCl | 40 mM, pH 7.2 |
| dA | 3 mM |
| dCTP | 5 mM |
| MgCl$_2$ | 6.5 mM |
| DTT | 2.5 mM |
| BSA | 50 µM |
| Enzyme: V 3 | 5 units/ml of reaction mixture |
| After three days, the following were added to this: | |
| poly [d(A–T)] | 1.5 A260 U |
| dGTP | 1 mM |
| dTTP | 1 mM |
| Temperature: 35° C. | |
| Duration of the reaction: 5 to 6 days | |
| Products: dAMP, dADP, dATP, poly d(A–T) | |

EXAMPLE 19

Reaction sequences utilizing the multifunctionality of the V 3 enzyme obtained in a manner as described in Example 1 were demonstrated by reacting a suitable quantity of the enzyme under the conditions described below.

| | |
|---|---|
| Buffer: tris-HCl | 50 mM, pH 7.5 |
| AMP | 1 mM |
| dGTP | 2 mM |
| Coenzyme B12 | 4 µM |
| DTT | 30 mM |
| BSA | 50 µg/ml |
| Enzyme: V 3 | 5 units/ml of reaction mixture |
| Once the AMP reduction to dAMP has attained equilibrium, 5 mM MgCl$_2$ are added to it. | |
| Products: dAMP, dADP, dATP | |

LITERATURE

1) Durham J. P., Ives D. H. Biochim.Biophys.Acta 228, 9–25, (1971)

2) Deilel M. R., Reznik R. B., Ives D. H. J.Biol.chem. 252 (22), 8240–44, (1977)

3) Deibel M. R., Ives D. H. J.Biol.Chem. 252 (22), 8235–38, (1977)

4) Ikeda S. Charkravarty R., Ives D. H. J.Biol.Chem. 261 (34), 15836–43, (1986)

5) Chakravarty R., Ikeda S., Ives D. H. Biochemistry 23, 6235–40, (1984)

6) Kirshner K., Bisswanger H. Annu.Rev.Biochem. 45, 143–66, (1976)

7) Harper & Row Proc.Acid.Res., pg. 284, (1966)

8) Lee M. Y. W. T. Biochemistry 27, 5188–93, (1988)

9) Hubscher U. Experiential 39 (1), 1–26, (1983)

10) Kaguni L. S., Lehman I. R. Biochim.Biophys.Acta 950, 87–101, (1988)

11) Hubscher U. TIBS September 1984, 390–93

12) Heilbronn R., Schlenhofer A. r. Int.J.Cancer 36, 85–91, (1985)

13) Focher F., Spadari S., Ginelli B. Nucl.Acid Res. 16(14), 6279–95, (1988)

14) Pfrogner N. Arch.Biochim.biophys. 119, 141–46, (1967)

15) Bernard A., Zaballos A., Salas M., Blanco L. EMBO J. 13(6), 4219–25, (1987)

16) Wong S. W., Wahl A. F., Uyan N. A., Aria N., Pearson B. E., Arai K., Korn D., Hunkapiller M., Wang T. S. F. EMBO J. 7 (1), 37–47, (1988)

17) Konberg A. DNA Replication (1980)

18) Konberg A. Supplement in DNA Replication (1982) Freeman W. H. and Co., San Francisco 19) Bialek G., Nasheuer J H. P., Goetz H., Beyhnke B., Grosse F. Biochim.Biophys,Acta 951, 290–97, (1988)

20) Brady T. G., O'Connel W. O. Biochim.Biophys.Acta 62, 216 (1962)

21) Oxford J. S., Coates A. R. M., Sia D. Il, Brown K., Asad S. Journal of Antimicrobial Chemotherapy 23, Suppl.A., 9–27, (1989)

22) Tisdale M., Larder B. A., Loewe D. J., Stammers D. J., Purifoy D. J. M., Ertl P., Bradley C., Kemp S., Darby G. K., Powell K. L. Journal of antimicrobial Chemotherapy 23, Suppl.A. 47–54 (1984)

23) Sanger F., Nicklen S., Golson A. R. Proc.Nat.Acad-.Sci. USA 74, 5463–67, (1977)

I claim:

1. A process for preparing deoxyribonucleotide(s), comprising the steps of:
    (A) providing an enzyme selected from the group consisting of polymerase, transferase, kinase, and deaminase; and
    (B) contacting said enzyme with at least one nucleotide in a reaction mixture,
    (C) with said enzyme, catalyzing the reduction of the ribosyl group of the nucleotide(s) to form said deoxyribonucleotide(s), and
    (D) optionally isolating said deoxyribonucleotide(s).

2. A process according to claim 1, wherein said enzyme of step (A) is selected from the group consisting of *E. coli* DNA polymerase I, *Micrococcus luteus* DNA polymerase, adenosine deaminase from calf spleen, and an enzyme having deoxyribosyltransferase activity obtainable from *Lactobacillus leichmannii*.

3. A process according to claim 2, wherein the enzyme having deoxyribosyltransferase activity is a nucleoside deoxyribosyltransferase from *Lactobacilius leichmannii*.

4. A process according to claim 3, wherein in step (B) the enzyme is also contacted with coenzyme B$_{12}$.

5. A process according to claim 4 or 3, wherein in step (B) the enzyme is further contacted with a deoxyribonucleoside triphosphate as an effector.

6. A process according to claim 2, wherein
    in step (A) said enzyme is adenosine deaminase from calf spleen, and
    in step (B) said at least one nucleotide is ADP or UDP and said enzyme is also contacted with NADPH and effectors.

7. A process according to claim 2, wherein
    in step (A) said enzyme is DNA polymerase from *Micrococcus luteus,* and
    in step (B) said at least one nucleotide is CTP.

8. A process according to claim 2, wherein
    in step (A) said enzyme is DMA polymerase I from *Escherichia coli,* and
    in step (B) said at least one nucleotide is ADP and said enzyme is also contacted with dGTP and NADPH.

9. A process according to claims 1 or 2, wherein the deoxyribonucleotide(s) produced is/are 2'-deoxyribonucleotide(s).

* * * * *